US009839411B2

United States Patent
Nishikubo (10) Patent No.: US 9,839,411 B2
(45) Date of Patent: Dec. 12, 2017

(54) ULTRASOUND DIAGNOSTIC APPARATUS PROBE HAVING LAMINATED PIEZOELECTRIC LAYERS ORIENTED AT DIFFERENT ANGLES

(75) Inventor: Yuichi Nishikubo, Kanagawa (JP)

(73) Assignee: KONICA MINOLTA MEDICAL & GRAPHIC, INC., Tokyo (JP)

( * ) Notice: Subject to any disclaimer, the term of this patent is extended or adjusted under 35 U.S.C. 154(b) by 0 days.

(21) Appl. No.: 13/371,617

(22) Filed: Feb. 13, 2012

(65) Prior Publication Data
US 2012/0220872 A1 Aug. 30, 2012

(30) Foreign Application Priority Data

Feb. 24, 2011 (JP) ................................ 2011-037980

(51) Int. Cl.
*A61B 8/00* (2006.01)
*A61B 8/14* (2006.01)
*B06B 1/06* (2006.01)

(52) U.S. Cl.
CPC ............ *A61B 8/4494* (2013.01); *B06B 1/064* (2013.01)

(58) Field of Classification Search
USPC ........................................................ 600/443
See application file for complete search history.

(56) References Cited

U.S. PATENT DOCUMENTS

| | | | | |
|---|---|---|---|---|
| 5,115,809 A * | 5/1992 | Saitoh | ...................... | B06B 1/064 310/334 |
| 5,417,219 A * | 5/1995 | Takamizawa | .......... | G01S 15/892 600/472 |
| 6,020,675 A * | 2/2000 | Yamashita et al. | ........... | 310/358 |
| 2003/0216646 A1 * | 11/2003 | Angelsen et al. | ............ | 600/437 |
| 2004/0049900 A1 * | 3/2004 | Emery et al. | ................. | 29/25.35 |
| 2005/0023934 A1 * | 2/2005 | Takeuchi | ............... | G10K 11/26 310/334 |
| 2007/0052329 A1 * | 3/2007 | Koc et al. | ..................... | 310/365 |

(Continued)

FOREIGN PATENT DOCUMENTS

JP 10-118065 5/1998
JP 2003-174698 6/2003
(Continued)

OTHER PUBLICATIONS

Multi-Layered PZT/Polymer Composites to Increase Signal-to-Noise Ratio and Resolution for Medical Ultrasound Transducers, David M. Mills, et al, pp. 961-971.

(Continued)

*Primary Examiner* — Serkan Akar
*Assistant Examiner* — Lisa Kinnard
(74) *Attorney, Agent, or Firm* — Lucas & Mercanti, LLP (57) ABSTRACT

An ultrasound probe includes a piezoelectric section to transmit and receive ultrasound, wherein the piezoelectric section includes a plurality of laminated piezoelectric layers each of which includes piezoelectric members and non-piezoelectric members both of which are arranged alternately in parallel to each other in an arrangement direction, and wherein the arrangement direction of the piezoelectric members and the non-piezoelectric members in at least one piezoelectric layer of the plurality of laminated piezoelectric layers is different from that in other one piezoelectric layer of the plurality of laminated piezoelectric layers.

9 Claims, 8 Drawing Sheets (56) References Cited

U.S. PATENT DOCUMENTS

| | | | | |
|---|---|---|---|---|
| 2007/0236106 A1* | 10/2007 | Koc | ............... | H01L 41/083 |
| | | | | 310/366 |
| 2008/0021328 A1* | 1/2008 | Habu et al. | ............... | 600/459 |
| 2008/0238259 A1* | 10/2008 | Osawa | ............... | B06B 1/0611 |
| | | | | 310/334 |
| 2009/0182237 A1* | 7/2009 | Angelsen et al. | ............... | 600/459 |
| 2012/0143063 A1* | 6/2012 | Robinson | ............... | A61B 8/00 |
| | | | | 600/472 |

FOREIGN PATENT DOCUMENTS

| | | |
|---|---|---|
| JP | 2007-185525 | 7/2007 |
| JP | 2009-061112 | 3/2009 |
| WO | WO 2010018525 A1 * | 2/2010 |

OTHER PUBLICATIONS

Multilayer 1-3 Piezocomposites—Theoretical and Experimental Study of Pillar Misalignment, J.F. Saillant, pp. 2007-2010.
The Effect of Pillar Misalignment on the Underwater Performance of High Frequency Multilayer 1-3 Piezocomposite Transducers with Acoustic Matching and Backing Layers, J. F. Saillant, pp. 630-633.
Japanese Office Action, Written Notice of Ground of Rejection, Patent Application No. 2011-037980. Date of Drafting Jun. 19, 2014 (3 pages).
English translation of Japanese Office Action, Written Notice of Ground of Rejection, Patent Application No. 2011-037980. Date of Drafting Jun. 19, 2014 (4 pages).

* cited by examiner

ULTRASOUND DIAGNOSTIC APPARATUS PROBE HAVING LAMINATED PIEZOELECTRIC LAYERS ORIENTED AT DIFFERENT ANGLES

This application is based on Japanese Patent Application No. 2011-037980 filed on Feb. 24, 2011, in Japanese Patent Office, the entire content of which is hereby incorporated by reference.

BACKGROUND OF THE INVENTION

Technical Field

The present invention relates to an ultrasound probe to transmit or receive ultrasound and an ultrasound diagnostic apparatus to produce an ultrasound image of the interior of an examined subject based on a reflective wave from the examined subject.

Background

Ultrasound is generally sound of at least 16000 Hz and makes it possible to nondestructively and harmlessly examine internal portions almost in real time, being thereby applied to various fields such as defect inspections and disease diagnoses. For one of these, there is an ultrasound diagnostic apparatus in which the interior of an examined subject is scanned with ultrasound, and then based on a received signal having been generated from a reflective wave of ultrasound propagated from the interior of the examined subject, the internal state in the examined subject is imaged. Such an ultrasound diagnostic apparatus has various features in medical use in which the ultrasound diagnostic apparatus is smaller and less expensive than other medical imaging devices, causes no exposure of radiation such as X-rays, and exhibits enhanced safety, as well as being able to display blood flow via application of the Doppler effect. Thereby, ultrasound diagnostic apparatus are being widely used in the circulatory system (for example, coronary arteries of the heart), the digestive system (for example, the gastrointestinal), internal medicine (for example, the liver, the pancreas, and the spleen), the urinary system (for example, the kidney and the bladder), and obstetrics and gynecology.

In an ultrasound diagnostic apparatus, an ultrasound probe to transmit and receive ultrasound with respect to an examined subject is used. Such an ultrasound probe is configured in such a manner that a plurality of piezoelectric elements to generate ultrasound by mechanical vibration based on a transmitted electric signal by use of a piezoelectric phenomenon and to produce a received electric signal by receiving a reflective wave of ultrasound generated via acoustic impedance mismatch in the interior of the examined subject are provided and the plurality of piezoelectric elements are arranged, for example, in a one-dimensional array manner or in a two-dimensional array manner.

Over recent years, research and development has been conducted with respect to harmonic imaging technology in which instead of a frequency (fundamental frequency) component of ultrasound having been transmitted into an examined subject from an ultrasound probe, using its harmonic component, an image of the internal state in the examined subject is formed. Harmonic imaging technology has various advantages such that compared with the level of a fundamental frequency component, sidelobe level is reduced and S/N ratio (Signal to Noise ratio) is improved to enhance contrast; frequency is increased and thereby beam width is reduced to enhance lateral resolution; sound pressure is reduced at a short distance and sound pressure variation is also reduced to suppress multi-reflection; and dampening beyond the focus is equivalent in a fundamental wave and compared with the case of a high-frequency wave as the fundamental wave, depth is increased (refer to, for example, Patent Documents 1 and 2).

When such a harmonic component is used, the bandwidth of an ultrasound probe itself needs to be increased, and therefore several techniques have been proposed. It is shown that, for example, in each piezoelectric layer constituting a 2-layer laminated-type piezoelectric transducer, a monolithic material (bulk) is changed to a composite material incorporating a piezoelectric member and a non-piezoelectric member to increase the bandwidth of ultrasound in transmission and reception (refer to Non-Patent Document 1). On the other hand, the importance of positioning with respect to lamination of a piezoelectric layer constituted of a composite material is shown (refer to Non-Patent Documents 2 and 3).

RELATED ART DOCUMENTS

Patent Document 1: Japanese Unexamined Patent Application Publication No, 10-118065
Patent Document 2: Japanese Unexamined Patent Application Publication No. 2007-185525
Non-Patent Document 1: IEEE Transactions on Ultrasonics, Ferroelectrics, and Frequency Control, Vol. 46, No. 4, pp. 961-971, July 1999
Non-Patent Document 2: 2003 IEEE Ultrasonics Symposium, pp. 2007-2010
Non-Patent Document 3: 2004 IEEE Ultrasonics Symposium, pp. 630-633

Non-Patent Documents 2 and 3 show that to realize excellent piezoelectric performance, positioning at the time when a piezoelectric layer constituted of a composite material in which a piezoelectric member and a non-piezoelectric member are alternately arranged is laminated is extremely critical, and when the gap between the positions of piezoelectric members in 2 piezoelectric layers to be laminated is several tens μm, the bandwidth and sensitivity, i.e., piezoelectric performance of ultrasound in transmission and reception is markedly degraded, depending, however, on the constitution of a composite material. Since the position gap amount in a laminated-type piezoelectric transducer in which such a composite material is laminated differs in an individual laminated-type piezoelectric transducer, piezoelectric performance also varies with respect to the individual laminated-type piezoelectric transducer.

On the other hand, the production method to control the relative position gap of a piezoelectric member at several tens pun or less when a piezoelectric layer is laminated is realized via lamination using, for example, an aligner. However, in an apparatus enabling to cover the following bonding process, expensive facility cost is required, and thereby the production of a laminated-type piezoelectric transducer, in which a composite material is laminated with a position gap of at most several tens μm, results in increased cost.

Therefore, it is extremely difficult to produce a laminated-type piezoelectric transducer in which a composite material is laminated so as to exhibit uniform piezoelectric performance at low cost with no variation, resulting in great difficulty in producing an ultrasound probe, eventually, an ultrasound diagnostic apparatus so as to have certain reproducibility and reliability as a product.

SUMMARY OF THE INVENTION

Therefore, an object of the present invention is to provide, at low cost, an ultrasound probe and an ultrasound diagnostic apparatus provided with a laminated-type piezoelectric transducer having small variation in piezoelectric performance.

The above object can be attained by the following structures.

Item (1) An ultrasound probe includes:
a piezoelectric section to transmit and receive ultrasound,
wherein the piezoelectric section includes a plurality of laminated piezoelectric layers each of which includes piezoelectric members and non-piezoelectric members both of which are arranged alternately in parallel to each other in an arrangement direction, and
wherein the arrangement direction of the piezoelectric members and the non-piezoelectric members in at least one piezoelectric layer of the plurality of laminated piezoelectric layers is different from that in other one piezoelectric layer of the plurality of laminated piezoelectric layers.

Item (2) In the ultrasound probe described in Item (1), the piezoelectric members and the non-piezoelectric members in the at least one piezoelectric layer are arranged so as to straddle the piezoelectric members and the non-piezoelectric members in the other one piezoelectric layer.

Item (3) In the ultrasound probe described in Item (1), when the number of the plurality of laminated piezoelectric layers is N, the arrangement direction in each of the plurality of laminated piezoelectric layers is different by an angle of (180/N) degrees from that in neighboring piezoelectric layers.

Item (4) In the ultrasound probe described in Item (1), the ultrasound probe further includes:
a plurality of piezoelectric sections as the piezoelectric section, wherein the plurality of piezoelectric sections are arrayed in one dimensional array form or two dimensional array form.

Item (5) In the ultrasound probe described in Item (4), the plurality of piezoelectric sections are arrayed in one dimensional array form, and the arrangement direction of the piezoelectric members and the non-piezoelectric members in at least one piezoelectric layer in the plurality of piezoelectric sections is parallel to an array direction in the one dimensional array form of the plurality of piezoelectric sections.

Item (6) A ultrasound diagnostic apparatus, includes:
a ultrasound probe including a piezoelectric section which transmits ultrasound to an examined subject, receives reflected ultrasound produced by the ultrasound reflected from the examined subject, and coverts the reflected ultrasound into electric signals;
an image processing section which produces a ultrasound image corresponding to an inside of the examined subject based on the electric signals converted by the piezoelectric section;
wherein the ultrasound probe is the ultrasound probe described in Item (1).

Item (7) In the ultrasound diagnostic apparatus described in Item (6), the ultrasound diagnostic apparatus includes:
a harmonic extracting section which extracts harmonic components contained in the electric signal converted by the piezoelectric section,
wherein the image processing section produces a ultrasound image corresponding to an inside of the examined subject based on the harmonic components.

Since the variation of piezoelectric performance due to the relative position gap of a laminated composite material is suppressed, an ultrasound probe and an ultrasound diagnostic apparatus provided with a laminated-type piezoelectric transducer having small variation in piezoelectric performance can be provided at low cost.

DETAILED DESCRIPTION OF THE PREFERRED EMBODIMENT OF THE INVENTION

The embodiment of the present invention will now be described with reference to the drawings but the present invention is not limited to the embodiment described below. Incidentally, in each figure, constitutions with the same symbols show the same constitutions and therefore description thereon will be omitted.

Figure 1:
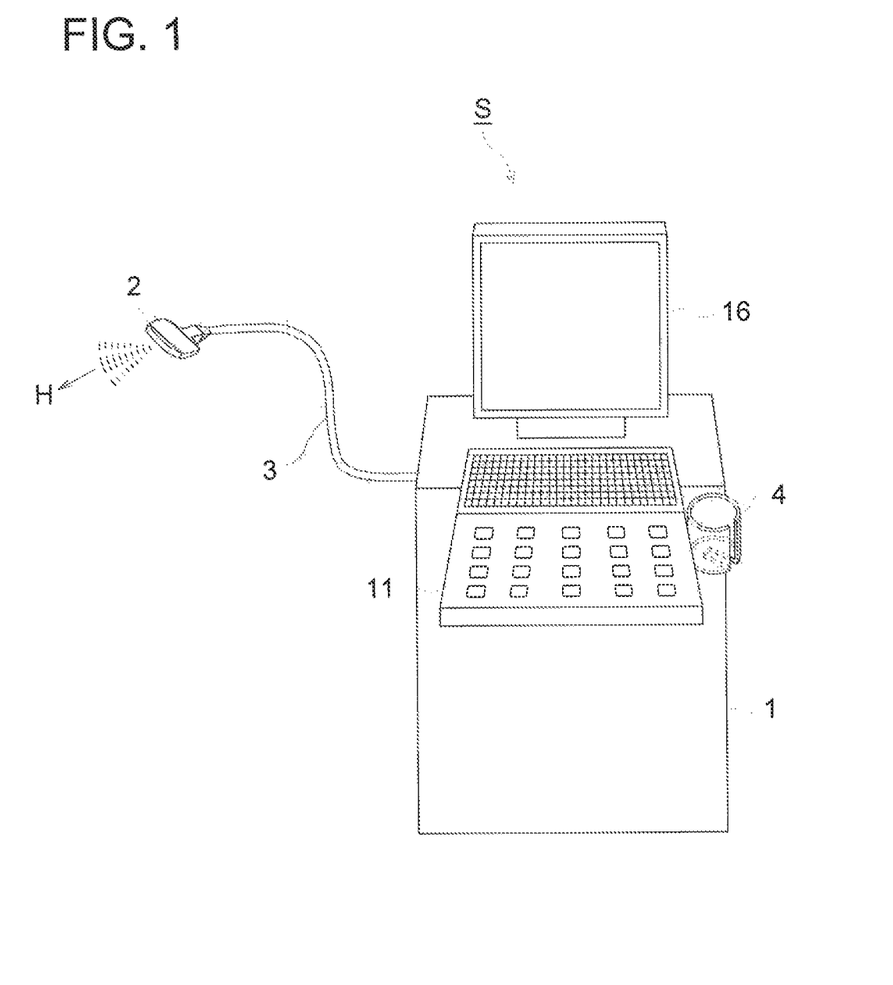
FIG. 1 is a schematic view showing the exterior constitution of an ultrasound diagnostic apparatus S according to an embodiment.
Figure 2:
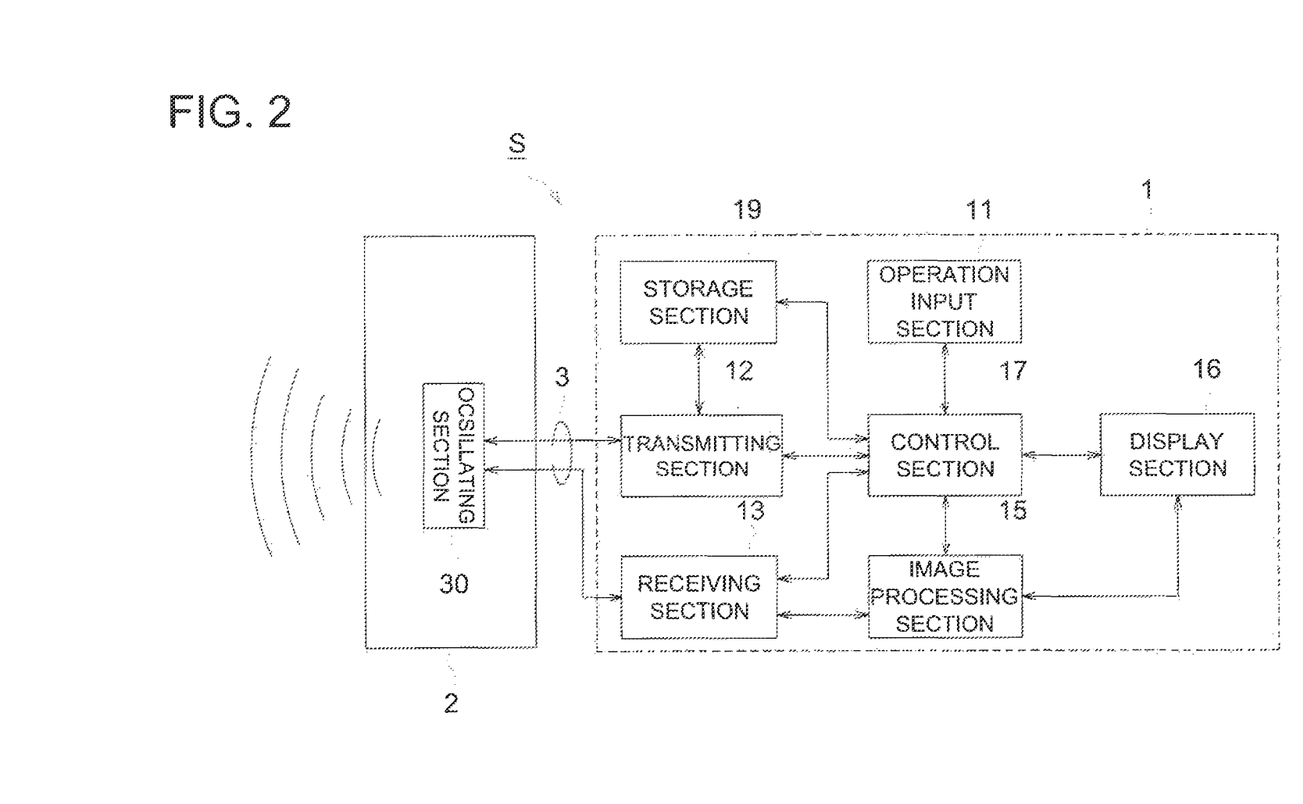
FIG. 2 is a block diagram showing the electric constitution of the ultrasound diagnostic apparatus S according to the embodiment.
Figure 3:
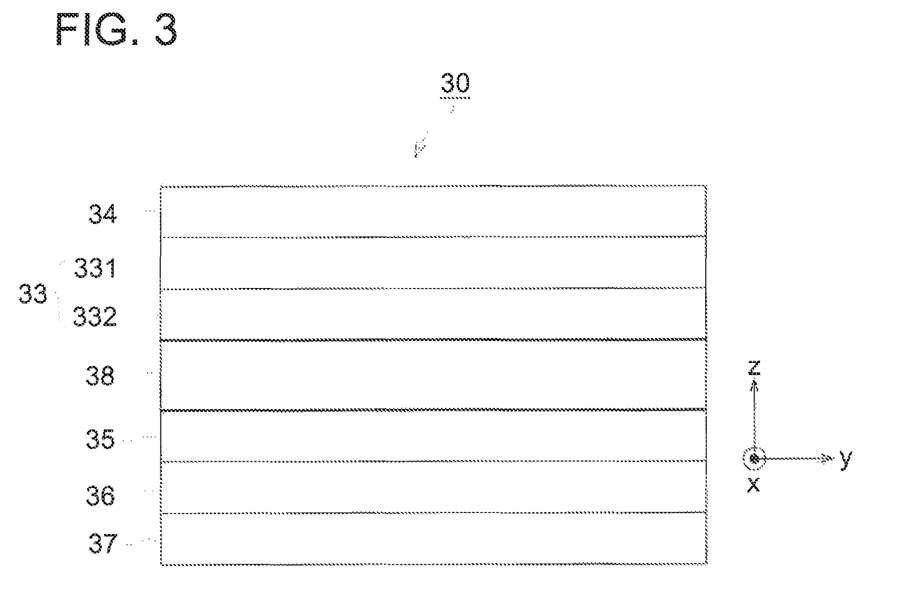
FIG. 3 is a schematic view showing the constitution of an ultrasound probe 2 of the ultrasound diagnostic apparatus S according to the embodiment.

FIG. 1 is a schematic view showing the exterior constitution of an ultrasound diagnostic apparatus S according to the embodiment. FIG. 2 is a block diagram showing the electric constitution of the ultrasound diagnostic apparatus S according to the embodiment. And, FIG. 3 is a schematic view showing the constitution of a vibrating section 30 provided for the ultrasound probe 2 of the ultrasound diagnostic apparatus S according to the embodiment.

As shown in FIG. 1 and FIG. 2, the ultrasound diagnostic apparatus S is configured in such a manner that there are provided an ultrasound probe 2 to transmit ultrasound to an not-shown examined subject H such as a living body and also to receive reflective ultrasound of the ultrasound having been reflected on the examined subject H; and an ultrasound diagnostic apparatus main body 1, connected to the ultrasound probe 2 via a cable 3, to transmit a transmission signal of an electric signal to the ultrasound probe 2 via the cable 3 to allow the ultrasound probe 2 to transmit ultrasound to an examined subject H and also to image the internal state in the examined subject H to form a medial image as an ultrasound image based on a reception signal of an electric signal, which has been produced by the ultrasound probe 2 in response to reflective ultrasound from the interior of the examined subject H, having been received by the ultrasound probe 2.

The ultrasound diagnostic apparatus main body 1 is provided with an ultrasound probe holder 4 to hold the ultrasound probe 2 when the ultrasound probe 2 is not used.

The ultrasound diagnostic apparatus 1 is configured in such a manner that, for example, as shown in FIG. 2, an operation input section 11, a transmitting section 12, a receiving section 13, an image processing section 15, a display section 16, a control section 17, and a storage section 19 are provided.

The operation input section 11 inputs, for example, commands to instruct diagnosis initiation and data such as personal information of an examined subject H, being, for example, an operation panel or a keyboard provided with a plurality of input switches.

The transmitting section 12 produces a transmission signal, being an electric signal, to drive a piezoelectric section 38 to be described later in response to the control of the control section 17, and further feeds the transmission signal to the piezoelectric section 38 in the ultrasound probe 2 via the cable 3 to allow the ultrasound probe 2 to generate ultrasound. The transmitting section 12 is constituted of, for example, a high-voltage pulse generator to produce high-voltage pulses.

The receiving section 13 receives a reception signal, being an electric signal, from the ultrasound probe 2 via the cable 3 in response of the control of the control section 17 and has a circuit serving as a harmonic extracting section to extract harmonic components from the electric signal and carry out a predetermined signal processing.

The image processing section 15 is a circuit to produce an ultrasound image based on a reception signal having been signal-processed in the receiving section 13 in response to the control of the control section 17. For example, a reception signal is subjected to envelope detection processing to produce a B-mode signal corresponding to the amplitude intensity of reflective ultrasound. Further, in the case of use of harmonic imaging technology, from harmonic components having been extracted by the harmonic extracting section of the receiving section 13, an ultrasound image of the interior of an examined subject is produced.

The storage section 19 incorporates a RAM or a ROM, in which programs used in the control section 17 are recorded and also templates of various kinds of image to be displayed in the display section 16 are recorded.

The control section 17 incorporates, for example, a microprocessor, a storage element, and peripheral circuits thereof, being a circuit to control the operation input section 11, transmitting section 12, receiving section 13, image processing section 15, display section 16, and storage section 19 in accordance with each function thereof for entire controlling of the ultrasound diagnostic apparatus S.

The display section 16 is a device to display an ultrasound image having been produced in the image processing section 15 in response to the control of the control section 16. The display section 16 is, for example, a display device such as a CRT display, an LCD, an EL display, and a plasma display or a printing device such as a printer.

The ultrasound probe 2 is provided with a vibrating section 30. The vibrating section 30 transmits ultrasound to an not-shown examined subject H such as a living body and also to receive reflective ultrasound from the examined subject H. As shown in FIG. 3, the vibrating section 30 has a piezoelectric section 38, an acoustic matching layer 33, an acoustic lens 34, an FPC 35, a backing layer 36, and a fixing plate 37.

The piezoelectric section 38 carries out signal conversion mutually between an electric signal and ultrasound using a piezoelectric phenomenon. The piezoelectric section 38 converts an electric signal of a transmission signal having been input from the transmitting section 12 of the ultrasound diagnostic apparatus main body 1 via the cable 3 into ultrasound for ultrasound transmission and also converts received reflective ultrasound into an electric signal to output this electric signal (reception signal) to the receiving section 13 of the ultrasound diagnostic apparatus main body 1 via the cable 3. The ultrasound probe 2 is brought into contact with an examined subject H, whereby ultrasound having been produced in the piezoelectric section 38 is transmitted into the examined subject H and then reflective ultrasound from the interior of the examined subject H is received by the piezoelectric section 38. As the piezoelectric material, an inorganic material or an organic material is used.

Details of the piezoelectric section 38 will be described later. The acoustic matching layer 33 has a first acoustic matching layer 331 and a second acoustic matching layer 332.

The acoustic matching layer 33 has an acoustic impedance value which is an intermediate value of the acoustic impedance of the piezoelectric section 38 and the acoustic impedance of an examined subject H, having, thereby, a function in which when ultrasound transmitted from the piezoelectric section 38 is transmitted to the examined subject H, reflective ultrasound generated in response to the difference in acoustic impedance between the piezoelectric section 38 and the examined subject H is reduced to efficiently transfer ultrasound having been generated in the piezoelectric section 38 to the examined subject H and also ultrasound having been reflected in the examined subject H to the piezoelectric section 38.

Since 2 acoustic matching layers, which are a first acoustic matching layer 331 and a second acoustic matching layer 332, are provided, compared with the case of one acoustic matching layer, the acoustic impedances of the piezoelectric section 38 and the examined subject H can be smoothly changed and the magnitude of reflective ultrasound generated between the piezoelectric section 38 and the examined subject H can be further reduced. Herein, it goes without saying that when at least 3 layers of an acoustic matching layer are formed so as for acoustic impedance to gradually approach the examined subject H from the piezoelectric section 38, the magnitude of reflective ultrasound can be further reduced.

The acoustic lens 34 functions to focus ultrasound transmitted from the piezoelectric section 38 toward a measurement site.

The FPC (flexible printed circuit) 35 is a flexible printed circuit board in which circuits to electrically control an ultrasound probe are formed.

The backing layer 36 is a member incorporating a material absorbing ultrasound and absorbs ultrasound emitted toward the backing layer 36 from the piezoelectric section 38.

The backing layer 36 is an ultrasound absorbing body capable of absorbing unnecessary ultrasound. As the backing material used for the backing layer 36, usable are rubber-based complex materials and resin complex materials in which powder exhibiting inorganic physical properties such as powder of a metallic compound such as tungsten oxide, titanium oxide, or ferrite or McCall glass powder is incorporated in a thermoplastic resin such as natural rubber, ferrite rubber, a silicon resin, an epoxy resin, vinyl chloride, polyvinyl butyral (PVB), an ABS resin, polyurethane (PUR), polyvinyl alcohol (PVAL), polyethylene (PE), polypropylene (PP), polyacetal (POM), polyethylene terephthalate (PETP), a fluorine resin (PTFE), polyethylene glycol, or polyethylene terephthalate-polyethylene glycol copolymer.

A preferable backing material is formed of a rubber-based complex material or an epoxy resin complex material and the shape thereof can be appropriately selected based on the shapes of a piezoelectric member and a probe head containing a piezoelectric member.

The thickness of the backing material is preferably about 1-10 mm, specifically preferably 1-5 mm.

The fixing plate 37 functions to fix a backing layer 36, to provide an ultrasound probe 2 with stiffness, and to perform fixing during fabrication.

Figure 4:
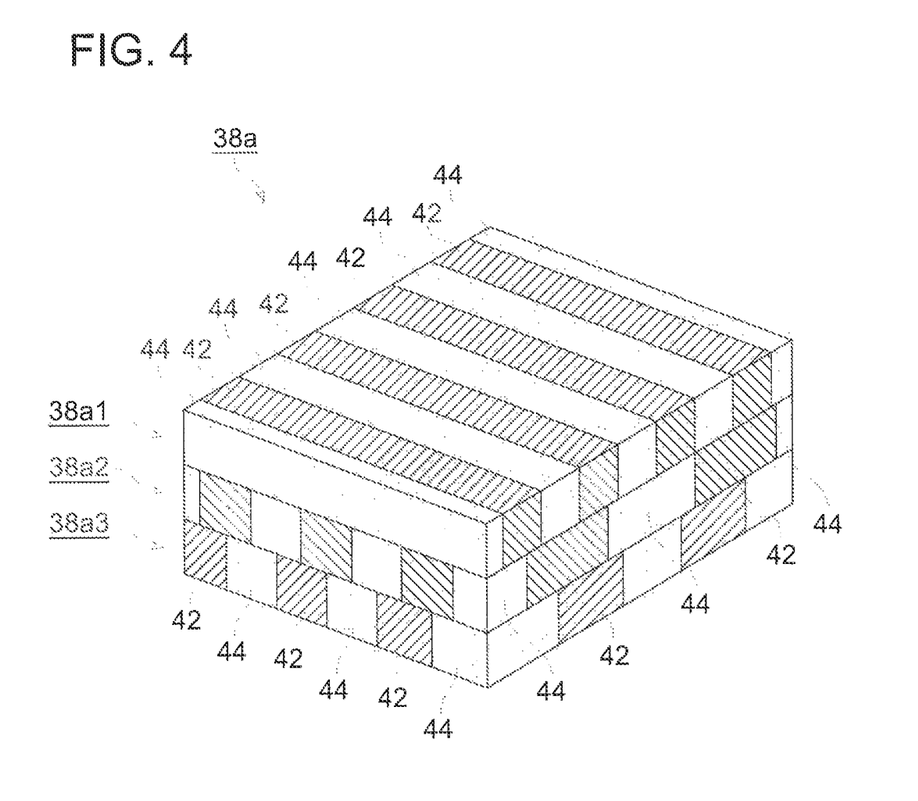
FIG. 4 is a perspective view of a piezoelectric section 38.

Next, the piezoelectric section 38 will be detailed. FIG. 4 is a perspective view of the piezoelectric section 38.

Figure 5:
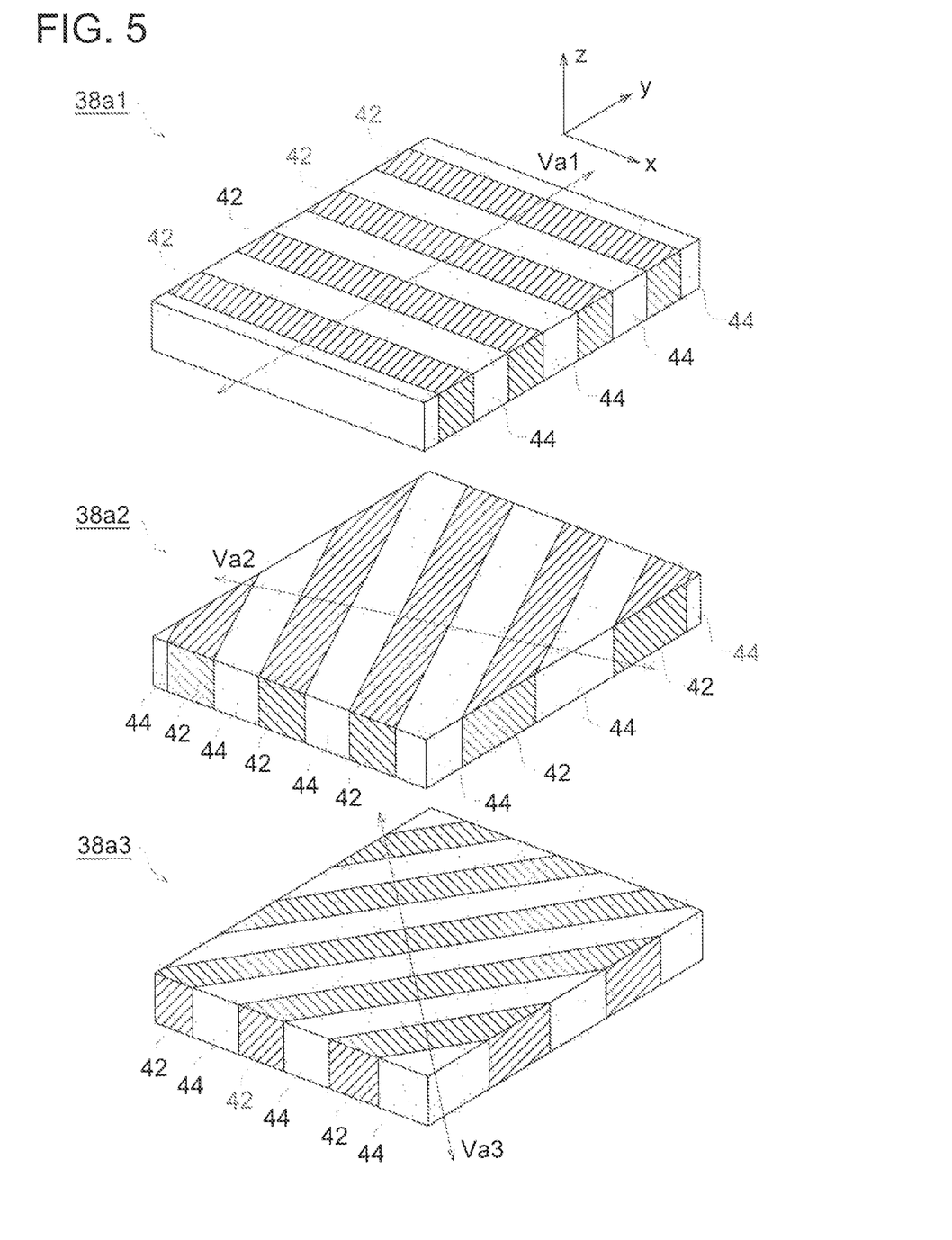
FIG. 5 is a perspective view of each of 3 piezoelectric layers 38a1, 38a2, and 38a3.

FIG. 5 is a perspective view of each of 3 piezoelectric layers 38a1, 38a2, and 38a3.

As shown in FIG. 4, the piezoelectric section 38a is a laminated-type piezoelectric transducer in which 3 piezoelectric layers 38a1, 38a2, and 38a3 are laminated. The piezoelectric layers 38a1, 38a2, and 38a3 are fixed by coating an adhesive on the interfaces laminated.

Each of the piezoelectric layers 38a1, 38a2, and 38a3 is a composite material (2-2 composite material) in which a piezoelectric member 42 and a non-piezoelectric member 44 are alternately arranged, and with a pitch t produced by a pair of the piezoelectric member 42 and the non-piezoelectric member 44, the piezoelectric member 42 and the non-piezoelectric member 44 are alternately arranged in line one-dimensionally with a periodicity in each predetermined direction.

As shown in FIG. 5, the piezoelectric layers 38a1, 38a2, and 38a3 each are arranged so that the arrangement direction of a piezoelectric member 42 and a non-piezoelectric member 44 differs from each other by 60 degrees.

In cases in which a piezoelectric layer 38a1, a piezoelectric layer 38a2, and a piezoelectric layer 38a3 are arranged in such a manner, even when an arrangement is made by reducing the positioning accuracy of each piezoelectric layer, the variation of the piezoelectric performance of the piezoelectric section 38a can be suppressed. Herein, the piezoelectric performance represents sensitivity and bandwidth.

Sensitivity refers to a collective term including the ratio of ultrasound intensity to electric power fed between electrodes during transmission (transmission sensitivity), the ratio of electric power obtained through the electrodes to ultrasound intensity having been received during reception (reception sensitivity), and the ratio of electric power obtained through the electrodes during reception to electric power fed between the electrodes during transmission (transmission and reception sensitivity).

Bandwidth refers to a collective term including the bandwidth of ultrasound of each order transmitted, the bandwidth of ultrasound of each order received, and the bandwidth of ultrasound of each order ranging from transmission to reception.

In the ease of use of the above harmonic imaging technology, to generate harmonics in an examined subject, it is necessary to sufficiently increase the sound pressure of ultrasound in the examined subject, and since harmonics contained in ultrasound received is weak, an ultrasound probe featuring enhanced transmission sensitivity and reception sensitivity, as well as small variation, is required. Further, since harmonics covering frequencies of integral multiples of the frequency of ultrasound transmitted need to be received, an ultrasound probe featuring adequately large bandwidth and small variation is required. The ultrasound probe of the present invention has small variation in the piezoelectric performance, i.e., sensitivity and bandwidth of the piezoelectric section 38a and thereby is specifically effective as an ultrasound probe used in harmonic imaging technology.

The reason why the variation of the piezoelectric performance of the piezoelectric section 38a, being a laminated-type piezoelectric transducer in which a plurality of composite materials are laminated, can be suppressed is described below.

In the case where as in the conventional technique, a plurality of piezoelectric layers are laminated so that the arrangement direction of a piezoelectric member 42 and a non-piezoelectric member 44 (hereinafter, referred to as the piezoelectric member arrangement direction) accords, when the relative angle and the relative position of the plurality of piezoelectric layers are shifted to a small extent, the area of a portion where the piezoelectric members 42 of the plurality of piezoelectric layers are overlapped with each other up and down is largely varied. In contrast, as shown in the above example, in the case where at least one of a plurality of piezoelectric layers is laminated so as to differ in piezoelectric member arrangement direction from another one of the plurality of piezoelectric layers, even when relative angle and relative position are shifted to a small extent, the variation of the area of a portion where the piezoelectric members 42 of the plurality of piezoelectric layers are overlapped with each other up and down is reduced, resulting in suppression of the variation of piezoelectric performance.

In this manner, to suppress the variation of piezoelectric performance due to the relative position gap of piezoelectric members, at least one of a plurality of piezoelectric layers is laminated so as to differ in piezoelectric member arrangement direction from another one of the plurality of piezoelectric layers (namely, in all the piezoelectric layers, any arrangement is not made so as for the piezoelectric member arrangement directions thereof to accord with each other). The number of laminated piezoelectric layers is not specifically limited. For example, in the case of a laminated-type piezoelectric transducer in which 2 layers of a piezoelectric layer are laminated, the 2 piezoelectric layers are laminated in piezoelectric member arrangement directions differing from each other. Further, in the case of a laminated-type piezoelectric transducer in which 3 layers of a piezoelectric layer are laminated, the 3 piezoelectric layers may be laminated in piezoelectric member arrangement directions differing from each other or it is possible that 2 piezoelectric layers are laminated in the same piezoelectric member arrangement direction and the remaining piezoelectric layer is laminated in a piezoelectric member arrangement direction differing from the above one. Still further, in the case of a laminated-type piezoelectric transducer in which 4 layers of a piezoelectric layer are laminated, (1) the 4 piezoelectric layers may be laminated in piezoelectric member arrangement directions differing from each other, (2) 3 piezoelectric layers are laminated in the same piezoelectric member arrangement direction and the remaining piezoelectric layer is laminated in a piezoelectric member arrangement direction differing from the above one, or (3) it is possible that 2 sets of a pair of piezoelectric layers in which the piezoelectric member directions thereof accord with each other are prepared and then lamination is performed with a difference in piezoelectric member arrangement direction between the 2 pairs.

In the case of lamination of N layers of a piezoelectric layer, when lamination is performed so as for the piezoelectric member arrangement directions thereof to differ from each other between neighboring piezoelectric layers by 180/N (°), the variation of the area of a portion where piezoelectric members 42 of a plurality of piezoelectric layers are overlapped with each other up and down can be further reduced in the case where the relative angle and the relative position of the piezoelectric layers are shifted to a small extent, and thereby the variation of piezoelectric performance can be more effectively suppressed. In the case of the example of FIG. 4, lamination is performed so that the angle θa1 of the piezoelectric member arrangement direction Va1 of the piezoelectric layer 38a1 and the piezoelectric member arrangement direction Va2 of the piezoelectric layer 38a2, the angle θa2 of the piezoelectric member arrangement direction Va2 of the piezoelectric layer 38a2 and the piezoelectric member arrangement direction Va3 of the piezoelectric layer 38a3, and the angle θa3 of the piezoelectric member arrangement direction Va3 of the piezoelectric layer 38a3 and the piezoelectric member arrangement direction Va1 of the piezoelectric layer 38a1 each are 60° (=180°/3).

Next, the case where the piezoelectric layer in the piezoelectric section 38 has 2 layers instead of 3 layers will be described.

Figure 6:
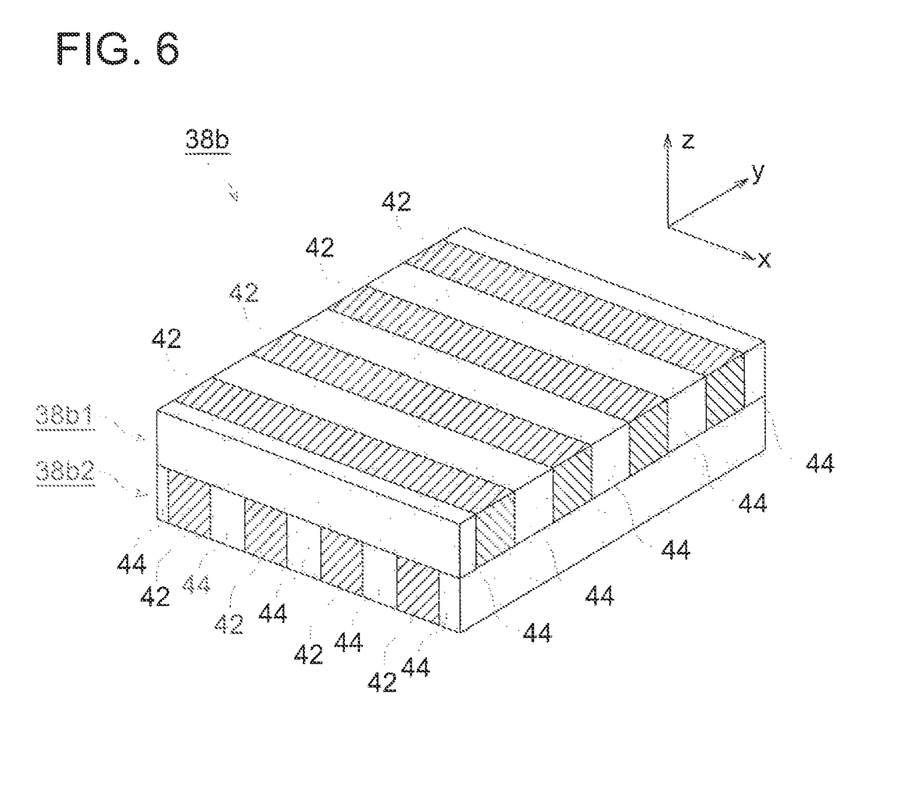
FIG. 6 is a perspective view of a piezoelectric section 38b containing 2 layers of a piezoelectric layer.

FIG. 6 is a perspective view of a piezoelectric section 38b containing 2 layers of a piezoelectric layer.

Figure 7:
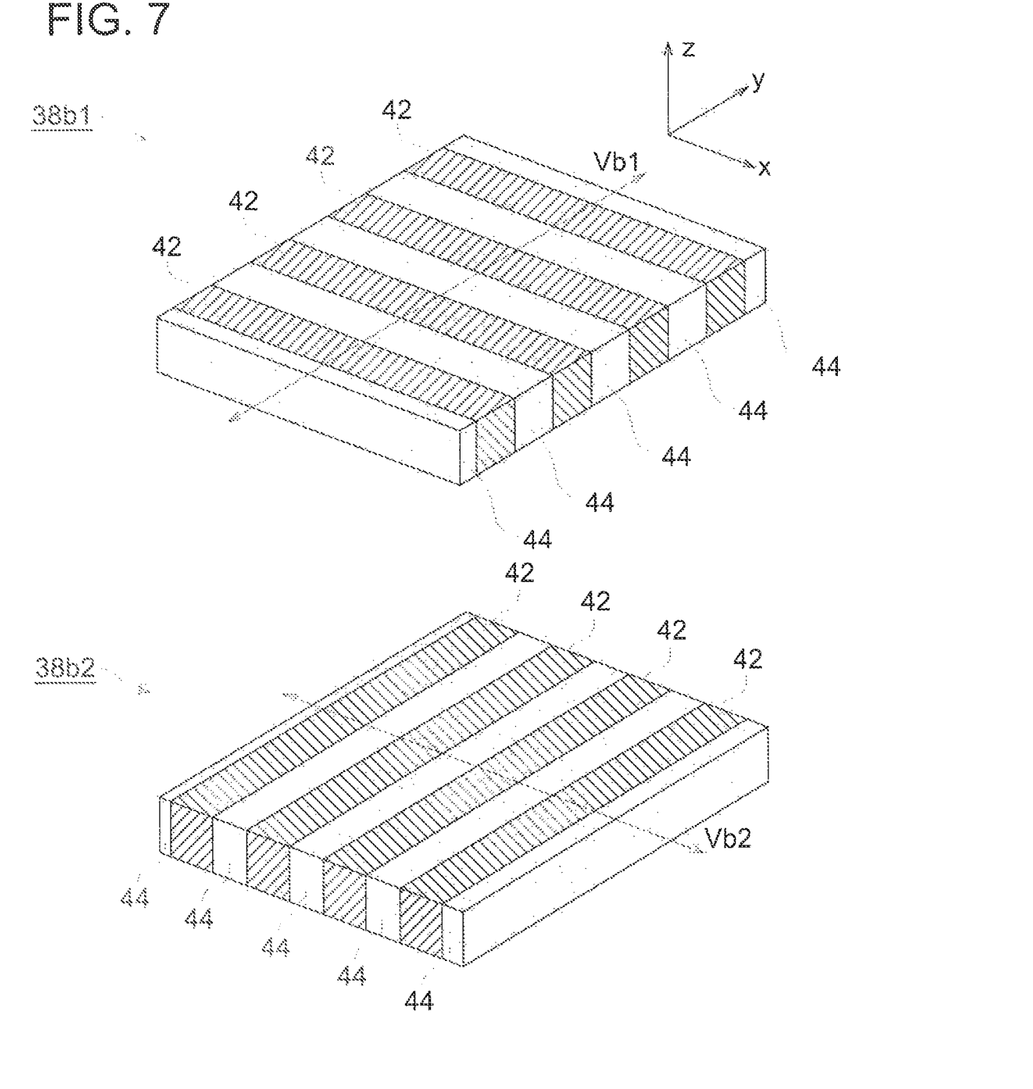
FIG. 7 is a perspective view of each of 2 piezoelectric layers 38b1 and 38b2.

FIG. 7 is a perspective view of each of 2 piezoelectric layers 38b1 and 38b2.

As shown in FIG. 6, the piezoelectric section 38b is formed by laminating two piezoelectric layers 38a1 and 38b2. The piezoelectric layers 38b1 and 38b2 are fixed by coating an adhesive on the interface thereof.

In each of the piezoelectric layers 38b1 and 38b2, a piezoelectric member 42 and a non-piezoelectric member 44 are alternately arrayed uniaxially in a one-dimensional manner with a periodicity of pitch t produced by a pair thereof.

As shown in FIG. 7, the piezoelectric layers 38b1 and 38b2 each are laminated so that the angle θb of the piezoelectric member arrangement direction Vb1 of the piezoelectric layer 38b1 and the piezoelectric member arrangement direction Vb2 of the piezoelectric layer 38b2 is 90° (=180°/2).

When the piezoelectric layer 38b1 and the piezoelectric layer 38b2 are arranged in such a manner, the area of the overlapping portion of the piezoelectric member 42 and the non-piezoelectric member 44 is reduced. Thereby, even when relative angle and relative position are shifted to a small extent, the variation of the area of a portion where the piezoelectric members 42 of the 2 piezoelectric layers are overlapped with each other up and down is reduced, resulting in suppression of the variation of piezoelectric performance.

Next, a production method of a piezoelectric section 38 being a laminated-type piezoelectric transducer in which a plurality of composite materials are laminated will be described with reference to the piezoelectric section 38a shown in FIG. 4 as an example.

The piezoelectric section 38a is produced using, for example, a dice and fill method.

FIG. 8 is a view illustrating the production method of a piezoelectric section 38a.

A non-piezoelectric member 44 is specifically a resin layer, and a filling agent filled between piezoelectric members 42 is preferably used.

Figure 8A:
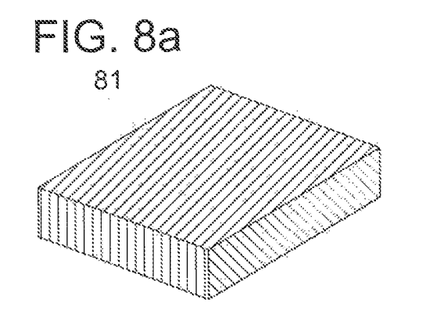
FIGS. 8a to 8f are schematic diagrams illustrating a production method of the piezoelectric section 38.

FIG. 8A shows a plate material 81 of PZT as a piezoelectric material. Other than this, piezoelectric materials usable as a piezoelectric member 42 include single crystal such as quartz, $LiNbO_3$, $LiTaO_3$, $KNbO_3$, or magnesium niobate-lead titanate solid solution, a thin film such as ZnO or AlN, a $Pb(Zr,Ti)O_3$-based fired body (PZT), a vinylidene fluoride polymer or copolymer, a vinylidene cyanate polymer or copolymer, a urea resin, an organic material containing fine particles of a non-fluorine-based resin such as polyester and a fluorine-based polymer such as a vinylidene fluoride polymer, and an electret in which a charge is injected into porous polypropylene.

Figure 8B:
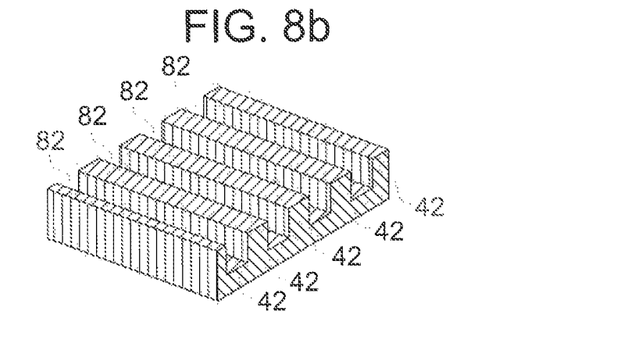

As shown in FIG. 8B, in a plate material 81 of PZT, grooves 82 having the same pitch are formed using a dicing saw. The grooves 82 are formed and thereby piezoelectric members 42 are arranged with the same pitch. Dicing is carried out employing a rectangular dicing blade having a thickness of at most the groove width.

Figure 8C:
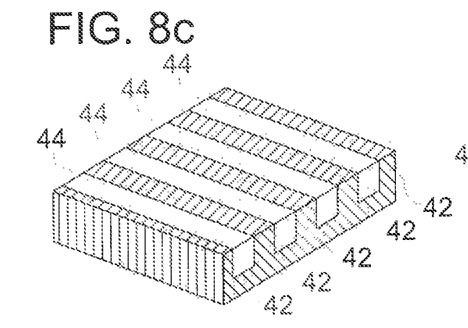

Subsequently, as shown in FIG. 8C, a resin is selected as a filling agent and then the filling agent is filled in the formed grooves 82 to form a non-piezoelectric member 44. Other than this, the filling agent used as the non-piezoelectric member 44 includes a general resin such as an epoxy resin or a silicon resin. For physical properties adjustment, other additives such as a filler may be added.

Figure 8D:
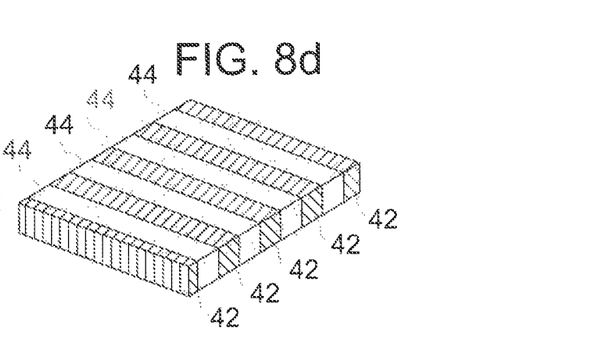

Then, as shown in FIG. 8D, PZT located below the bottom of the non-piezoelectric member 44 in the plate material 81 is eliminated by grinding to obtain a piezoelectric layer in which the piezoelectric member 42 and the non-piezoelectric member 44 are alternately arranged in line.

Figure 8E:
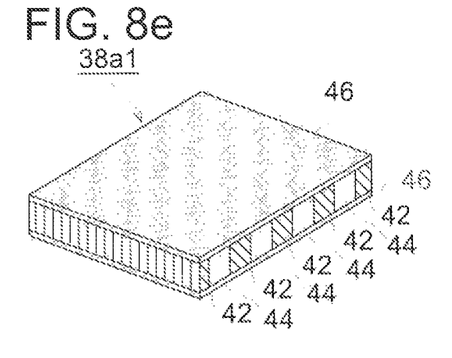

Thereafter, as shown in FIG. 8E, electrodes 46 are formed on both sides of the thus-produced piezoelectric layer to obtain one piezoelectric layer 38a1. The electrodes 46 are formed, for example, via film formation of a conductive body such as metal using a vacuum film forming method. The electrodes 46 are formed separately on both surfaces of each piezoelectric layer of the plurality of laminated piezoelectric layers 38a1, 38a2 and 38a3 so as to straddle over a plurality of the arranged piezoelectric members 42 and non-piezoelectric members 44 to function as common electrodes to a plurality of the piezoelectric members 42 arranged in the piezoelectric layer 38a.

Piezoelectric layers 38a2 and 38a3 are produced in the same manner as in the production method of the piezoelectric layer 38a1 except that the dicing angle is inclined by 60° to each other.

Figure 8F:
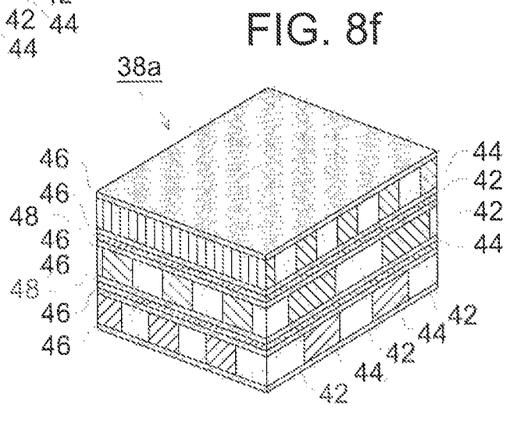

Then, as bonding layers 48 of an adhesive are formed between the obtained piezoelectric layers 38a1, 38a2, and 38a3, the piezoelectric layers 38a1, 38a2, and 38a3 are laminated and bonded to obtain a piezoelectric member 38a as shown in FIG. 8F. The used adhesive includes a UV curable adhesive and a thermally curable adhesive.

Herein, in the above description, the piezoelectric layers 38a1, 38a2, and 38a3 each are produced with the same size, followed by bonding and lamination to obtain a piezoelectric section 38a as a finished product. However, when these are produced in advance with a larger size than a finished product, followed by cutting via dicing, piezoelectric sections 38a are obtained as plural finished products, whereby mass-production can be realized at reduced cost.

Incidentally, when the thickness of the bonding layer 48 formed of an adhesive is excessively large, adverse effects on the vibration of a piezoelectric section such as a decrease in resonance frequency become significant. Therefor, the thickness is preferably as small as possible in the range where bonding properties are not adversely affected. For example, in an ultrasound probe for medical use, when transmission and reception of ultrasound of a frequency of about 1 MHz-20 MHz is carried out, the thickness of the bonding layer 48 is preferably at most 3 μm, more preferably at most 2 μm.

Further, it is preferable that a piezoelectric layer being a composite material be laminated to form a piezoelectric section, followed further by element dividing via dicing to give an ultrasound probe in which a plurality of piezoelectric sections are arranged in one-dimensional array manner or a two-dimensional array manner. An ultrasound probe, in which a plurality of piezoelectric sections are arranged in an array manner in this way, is referred to as a ID array element or a 2D array element. When beamforming to drive each piezoelectric section at predetermined timing is carried out, the direction where ultrasound is transmitted and received and focus position can be controlled.

An ultrasound probe in which a plurality of piezoelectric sections are arranged in a one-dimensional array manner is more preferably configured so that of a plurality of laminated piezoelectric layers, the symmetrical axis of the piezoelectric member arrangement direction of at least one set of piezoelectric layers is parallel to the array direction of the piezoelectric section. Further, when the plurality of piezoelectric sections are arrayed in one dimensional array form, it is preferable that the arrangement direction of the piezoelectric members and the non-piezoelectric members in at least one piezoelectric layer in the plurality of laminated piezoelectric layers is parallel to an array direction in the one dimensional array form of the plurality of piezoelectric sections. Furthermore, when the number of the plurality of laminated piezoelectric layers is N, it is preferable that the arrangement direction in each of the plurality of laminated piezoelectric layers is different by an angle of (180/N) degrees from that in neighboring piezoelectric layers thereof. Such a configuration makes it possible that the distribution of the piezoelectric performance of each piezoelectric section in the elevation direction (the direction vertical to the array direction of the piezoelectric section) is allowed to have a symmetrical shape to the center to realize an ultrasound probe exhibiting small sidelobe level.

Further, as the thickness of each piezoelectric layer decreases, the contraction stress generated during grinding or thermal curing of a non-piezoelectric section exceeds the stiffness of a piezoelectric member, whereby distortion becomes significant. The degree of generated distortion depends on the piezoelectric member arrangement direction and the dimension (for example, the length of the long axis direction) of a piezoelectric member. However, when as shown in the present invention, at least one of a plurality of piezoelectric layers is laminated so as to differ in piezoelectric member arrangement direction from another one of the plurality of piezoelectric layers, the degree of generated distortion can be reduced. Thereby, fabrication yield is increased and distortion underlying even after fabrication is reduced, resulting in maintenance of stable quality.

Examples

[Production of Ultrasound Probe 2a]

In the order from the bottom layer, lamination and bonding was carried out using a fixing plate, a backing layer, and epoxy-based adhesive DP-460 (produced by 3M Co.) at a pressure of $2.94 \times 10^6$ Pa and 50° C. for 4 hours so as to result in a patterned FPC.

Thereafter, a plate material of PZT (ceramic) was fabricated and formed into ceramic/resin=35/35 (μm) via a dice and fill method to produce a 2-2 composite material, and therefrom, with respect to 3 types including a type (type a1) in which the arrangement direction of the ceramic and the resin (piezoelectric member arrangement direction) was parallel to the short axis direction; and types (type a2 and type a3) in which the piezoelectric member arrangement direction was rotated by +60° and −60° from the short axis, thin plates of a size of 5.1 mm×52.5 mm×100 μm each were cut out. As the resin, E SET L EPOXY RESIN (produced by Konishi Co., Ltd.) was used. On the front and back surface of each composite material of the 3 types, electrodes were formed, and using epoxy-based adhesive DP-460 (produced by 3M Co.), initially, type a2 and type a3 were bonded together and then type a1 was laminated and bonded under the same condition. Thereafter, a first and a second acoustic matching layer were laminated and bonded under the same condition, followed by dicing using a blade having a thickness of 30 μm with a pitch of 0.15 mm in the longitudinal direction. Further, an insulating layer of about 3 μm was provided on the surface using paraxylylene and then thereon, an acoustic lens was bonded. Thereafter, a connector was connected to the FPC and the thus-produced ultrasound transducer was placed in a case to produce ultrasound probe 2a. Such steps were repeated to produce 20 ultrasound probes 2a in total.

[Production of Ultrasound Probe 2b]

In the order from the bottom layer, lamination and bonding was carried out using a fixing plate, a backing layer, and epoxy-based adhesive DP-460 (produced by 3M Co.) at a pressure of $2.94 \times 10^6$ Pa and 50° C. for 4 hours so as to result in a patterned FPC.

Thereafter, a plate material of PZT was fabricated and formed into ceramic/resin=35/35 (μm) via a dice and fill method to produce a 2-2 composite material, and therefrom, with respect to 2 types including a type (type b1) in which the piezoelectric member arrangement direction was parallel to the short axis direction; and a type (type b2) in which the piezoelectric member arrangement direction was rotated by +90° from the short axis, thin plates of a size of 5.1 mm×52.5 mm×100 μm each were cut out. As the resin, E SET L EPOXY RESIN (produced by Konishi Co., Ltd.) was used. On the front and back surface of each composite material of the 2 types, electrodes were formed, and using epoxy-based adhesive DP-460, lamination and bonding were carried out under the same condition. Thereafter, a first and a second acoustic matching layer were laminated and bonded under the same condition, followed by dicing using a blade having a thickness of 30 μm with a pitch of 0.07 mm in the longitudinal direction. Further, an insulating layer of about 3 μm was provided on the surface using paraxylylene and then thereon, an acoustic lens was bonded. Thereafter, a connector was connected to the FPC and the thus-produced ultrasound transducer (vibrating section) was placed in a case to produce ultrasound probe 2b. Such steps were repeated to produce 20 ultrasound probes 2b in total.

[Production of Comparative Probes A and B]

As a composite material, 3 sheets of a type (type a1) in which the piezoelectric member arrangement direction was parallel to the short axis direction were used to produce 20 comparative probes A via lamination and bonding in the same manner as for the ultrasound probe 2a, and as a composite material, 2 sheets of a type (type b1) in which the piezoelectric member arrangement direction was parallel to the short axis direction were used to produce 20 comparative probes B via lamination and bonding in the same manner as for ultrasound probe 2b.

When comparative probe B was produced, the side of the piezoelectric section after lamination and bonding was observed using a stereomicroscope to determine the position gap amount of 2 sheets of the composite material, and thereby the average value, the maximum value, and the standard deviation were 0.11 mm, 0.18 mm, and 0.05 mm, respectively. Herein, in all produced ultrasound probes (ultrasound probes 2a and 2b and comparative probes A and B), the alignment accuracy during composite material lamination is equal and thereby it is conceivable that in all the ultrasound probes, position shifting occurs to a similar extent.

[Evaluation of Ultrasound Probes 2a and 2b]

Each of ultrasound probes 2a and 3b and comparative probes A and B was placed in degassed air in the state where a pulser-receiver (PAN AMETRICS-NDT MODEL 5900PR, produced by Olympus Corp., with an input impedance of 5000Ω) and an oscilloscope (TPS5032, produced by Tektronics Inc.) were connected together and a metal reflective plate was arranged on the ultrasound emitting surface side.

Short-pulse ultrasound having adequately wide band frequency components was transmitted into the water and then ultrasound having been reflected by the reflective plate was received, followed by conversion into an electric signal to confirm its voltage waveform using the oscilloscope.

The distance of ultrasound probes 2a and 2b from the reflective plate was allowed to be 6 mm and then alignment is carried out so as for the effective value of the voltage waveform to be maximized.

After alignment, ultrasound was transmitted and received at the above frequency and then from the intensity of an obtained electric signal, transmission and reception sensitivity was evaluated. Evaluation was conducted in such a manner that when of the ultrasound probes (20 each) of each case, one exhibiting largest sensitivity was designated as the reference, the standard deviation of the sensitivity decreasing amounts (dB) of the 20 ultrasound probes in each case was determined. The results are shown in Table 1.

TABLE 1

| | Layer Number of Composite Material Sensitivity | Decreasing Amount Standard Deviation (dB) |
|---|---|---|
| Ultrasound Probe 2a | 3 | 0.9 |
| Comparative Prove A | 3 | 2.5 |
| Ultrasound Probe 2b | 2 | 0.5 |
| Comparative Prove A | 2 | 2.5 |

As shown in Table, the standard deviation of the sensitivity decreasing amount of ultrasound probe 2a of a 3 layer laminated-type is 0.9 dB, resulting in sufficient suppression, compared with 2.5 dB with respect to comparative probe A of the same 3 layer laminated-type. Further, the standard deviation of the sensitivity decreasing amount of ultrasound probe 2b of a 2 layer laminated-type is 0.5 dB, resulting in sufficient suppression, compared with 2.5 dB with respect to comparative probe B of the same 2 layer laminated-type. It turns out that in ultrasound probe 2a and ultrasound probe 2b, the variation of piezoelectric performance due to the relative position gap of laminated composite materials is suppressed in this manner and therefore, when ultrasound probe 2a or ultrasound 2b is used, an ultrasound probe and an ultrasound diagnostic apparatus provided with a laminated-type piezoelectric transducer exhibiting small variation in piezoelectric performance can be provided at low cost.

What is claimed is:

1. An ultrasound probe, comprising:
 a piezoelectric section configured to transmit ultrasound in a transmission direction toward an examined subject and to receive ultrasound reflected from the examined subject, the piezoelectric section having a plurality of laminated piezoelectric layers including at least a first piezoelectric layer and a second piezoelectric layer laminated in the transmission direction,
 wherein each piezoelectric layer of the plurality of laminated piezoelectric layers includes elongated members, each of the elongated members extends in an elongated direction, the elongated members of the each piezoelectric layer include piezoelectric elongated members and non-piezoelectric elongated members alternatingly arranged side-by-side in an arrangement direction, wherein the elongated direction of each of the elongated members in the each piezoelectric layer are parallel to each other, and each of the elongated members is a single continuous element extending across an entire length of the each piezoelectric layer in the elongate direction,
 wherein the plurality of piezoelectric sections are arrayed in one dimensional array form, and the arrangement direction of the piezoelectric elongated members and the non-piezoelectric elongated members in at least one piezoelectric layer in the plurality of laminated piezoelectric layers is parallel to an array direction in the one dimensional array form of the plurality of piezoelectric sections; and
 wherein when the number of the plurality of laminated piezoelectric layers is N, the arrangement direction in each of the plurality of laminated piezoelectric layers is differently oriented by an angle of (180/N) degrees from that in neighboring piezoelectric layers thereof; and
 a pair of sheet electrodes disposed separately on both surfaces of the each piezoelectric layer of the plurality of laminated piezoelectric layers,
 wherein each of the sheet electrodes straddles both the piezoelectric elongated members and the non-piezoelectric elongated members arranged in the piezoelectric layer, wherein the sheet electrodes are common electrodes for the piezoelectric elongated members of the each piezoelectric layer.

2. The ultrasound probe described in claim 1, wherein when the number of the plurality of laminated piezoelectric layers is N, the arrangement direction in each of the plurality of laminated piezoelectric layers is differently oriented by an angle of (180/N) degrees from that in neighboring piezoelectric layers thereof.

3. The ultrasound probe described in claim 1, further comprising:
 a plurality of piezoelectric sections as the piezoelectric section, wherein the plurality of piezoelectric sections are arrayed in a one dimensional array form or a two dimensional array form.

4. The ultrasound probe described in claim 3, wherein the plurality of piezoelectric sections are arrayed in the one dimensional array form, and the arrangement direction of the piezoelectric elongated members and the non-piezoelectric elongated members in at least one piezoelectric layer in the plurality of laminated piezoelectric layers is parallel to an array direction in the one dimensional array form of the plurality of piezoelectric sections, and
 wherein when the number of the plurality of laminated piezoelectric layers is N, the arrangement direction in each of the plurality of laminated piezoelectric layers is differently oriented by an angle of (180/N) degrees from that in neighboring piezoelectric layers thereof.

5. An ultrasound diagnostic apparatus, comprising:

the ultrasound probe of claim 1 including a piezoelectric section which transmits ultrasound to an examined subject, receives reflected ultrasound produced by the ultrasound reflected from the examined subject, and converts the reflected ultrasound into electric signals;

an image processing section which produces an ultrasound image corresponding to an inside of the examined subject based on the electric signals converted by the piezoelectric section.

6. The ultrasound diagnostic apparatus described in claim 5, further comprising:

a harmonic extracting section which extracts harmonic components contained in the electric signal converted by the piezoelectric section, wherein the image processing section produces an ultrasound image corresponding to an inside of the examined subject based on the harmonic components.

7. The ultrasound probe described in claim 1, wherein the arrangement direction of the piezoelectric elongated members and the non-piezoelectric elongated members in the each piezoelectric layer of the plurality of laminated piezoelectric layers is only a single direction.

8. The ultrasound probe described in claim 1, wherein the plurality of laminated piezoelectric layers consists of the first piezoelectric layer, the second piezoelectric layer, and a third piezoelectric layer, the elongated direction of the elongated members of the third piezoelectric layer is a third elongated direction, and the third elongated direction differs from each of the first elongated direction and the second elongated direction by 60 degrees.

9. The ultrasound probe described in claim 1, wherein the plurality of laminated piezoelectric layers consists of the first piezoelectric layer and the second piezoelectric layer, and the first elongated direction differs from the second elongated direction by 90 degrees.

* * * * *